United States Patent [19]

Cribbs et al.

[11] 4,172,386
[45] Oct. 30, 1979

[54] VIDEO A-TRACE DISPLAY SYSTEM FOR ULTRASONIC DIAGNOSTIC SYSTEM

[75] Inventors: Robert W. Cribbs, Placerville; John E. Mahony, Sacramento, both of Calif.

[73] Assignee: Litton Industrial Products, Inc., Beverly Hills, Calif.

[21] Appl. No.: 848,987

[22] Filed: Nov. 7, 1977

[51] Int. Cl.$^2$ .......................................... G01N 29/04
[52] U.S. Cl. .................................................... 73/618
[58] Field of Search .......................... 73/609, 618–626; 128/2 V

[56] References Cited

U.S. PATENT DOCUMENTS

| | | | |
|---|---|---|---|
| 3,856,985 | 12/1974 | Yokoi et al. | 73/629 X |
| 3,954,098 | 5/1976 | Dick et al. | 73/621 X |
| 4,058,001 | 11/1977 | Waxman | 73/620 |

OTHER PUBLICATIONS

S. Lees et al., Donar: A Computer Processing System to Extend Ultrasonic Pulse-Echo Testing, Ultrasonics, Jul. 1973, pp. 165–173.

*Primary Examiner*—Anthony V. Ciarlante
*Attorney, Agent, or Firm*—Robert A. Seldon

[57] ABSTRACT

A method and circuitry are disclosed for displaying the A-Trace of ultrasonic reflections on a video screen. The disclosed system provides means for writing pulse reflection data into memory, and means for selectively accessing the memory to place the data on the screen in graphical form. The data is stored and accessed in a format which is compatible with the scan pattern associated with the video display.

9 Claims, 11 Drawing Figures

VIDEO A-TRACE DISPLAY SYSTEM FOR ULTRASONIC DIAGNOSTIC SYSTEM

BACKGROUND OF THE INVENTION

A. Field of the Invention

This invention relates to ultrasonic diagnostic systems such as those used in the medical field and, more particularly to the displaying of the ultrasonically derived information. More specifically, this invention provides both a technique and apparatus for the video displaying of the A-trace.

The A-trace is the graphically-depicted information derived from the ultrasonic pulse-echo emerging from the examined body. As is known in the art, pulse reflections occur when the ultrasonic transmitted pulse, transmitted into the examined body via a transducer, encounters a discontinuity in media defining the propogation path. The magnitude of the reflection is proportional to the difference in the media densities. The echo amplitude is typically graphically represented as the ordinate value, while the echo return time (indicative of body depth) is reproduced on the abscissa. Accordingly, one may, by viewing the A-trace, determine the depth into the body of each discontinuity in the pulse-propogation path and the type of media transition. With one's knowledge of the theoretical internal structure of the body (or, in the case of medical diagnostics, the human physiology) one may identify the locations of various structural components (or organs).

B. Summary of the Prior Art

Conventional ultrasonic systems have employed oscilloscopes as the A-trace display means. Earlier systems employed two oscilloscopes, the second of which was dedicated to the display of images derived by subjecting the pulse-echo signal to one of several known signal-processing techniques. The oscilloscope possessed several inherent weaknesses, however, which led to the subsequent use of TV monitors for displaying the processed image. First, oscilloscopes offered poor display visability. Secondly, oscilloscopes having storage capability were expensive. Thirdly, oscilloscopes cannot provide highly desirable alphanumeric information, such as patient-identifying data. Additionally, the use of a TV monitor permitted the use of video tape, and the ability to drive several monitors from a single source, both of which are economically beneficial. The A-trace, however, continued to be displayed on an oscilloscope, necessitating the use of two display devices. If permanently recorded images were desired, two cameras, or alternately, a single relocatable camera, were necessary.

SUMMARY OF THE INVENTION

The present invention is a video A-trace system, for use with ultrasonic diagnostic instruments, which overcomes the limitations set forth above. The system basically comprises a memory into which data representative of sensed pulse-echo amplitudes sampled at discrete intervals subsequent to pulse launching are stored. The data is subsequently retrieved at a rate compatible with the scan frequencies of the video monitor used and converted to signals compatible with the beam-modulating circuitry of the monitor.

Further details concerning the invention are set forth in the following Description of the Preferred Embodiment of which the following drawing is part.

BRIEF DESCRIPTION OF THE DRAWING

In the drawing,

FIG. 1 A-C is a pictorial representation of video A-trace displays,

DESCRIPTION OF THE PREFERRED EMBODIMENT

Figures 1, 2A:
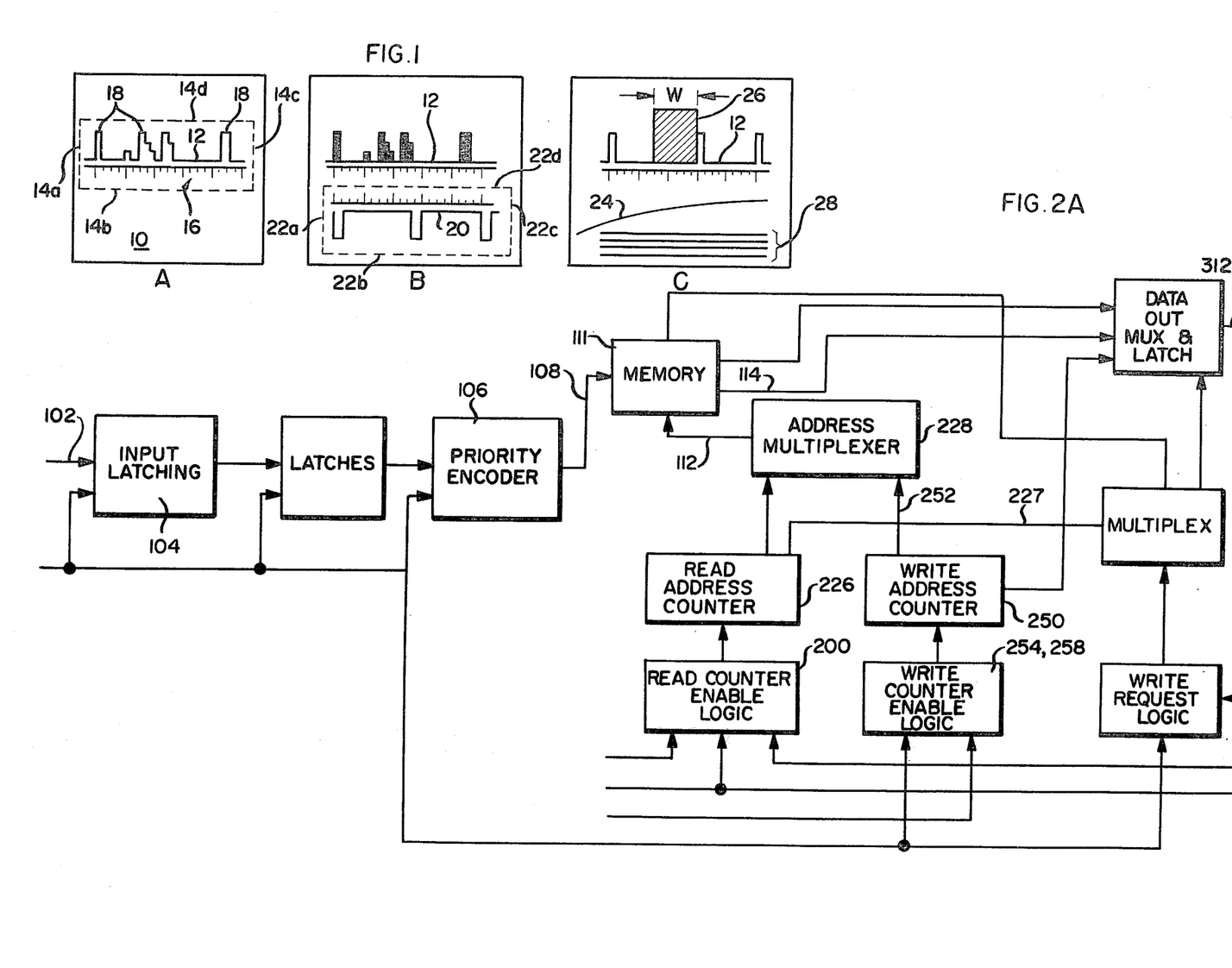
FIGS. 2A and 2B form a block diagram representation of the sytem.

FIG. 1 is a pictoral representation of a video display of the A-trace provided by the system hereinafter described and shows a photosensitive viewing screen 10 thereof having an A-trace 12 displayed thereon within a display area defined by dotted lines 14a–d. A comb marker 16 forms the abscissa of the A-trace and denotes return time or, correspondingly, the depth into the body of the propogation path discontinuity which generated the reflection. The amplitude of the reflection is represented by the peak value of the pulses 18.

Additionally displayed on the video screen is a caliper 26 whose horizontal position on the screen and whose width W, may be adjusted as hereinafter described by a human operator so as to accurately measure the pulse width of any of the reflections 18. As will also be explained, the measured widths may be visually displayed within several lines of alpha numeric characters 28 and conveniently placed at the bottom of the viewing screen.

Also displayed is a graphic representation of the Time Gain Control curve 24. The Time Gain Control curve, or TGC curve, is a graphic representation of the time-dependent gain of the ultrasonic receiver which increases with increasing return time to compensate for the attenuation of late arriving reflections from deep within the body.

The foregoing displays have not heretofore been presented on standard video display. During the following description, it is convenient to assume that the video displays utilize the standard raster scanning pattern known in the art, although it will be obvious that other scanning patterns may be equally utilized. However, the use of the standard raster pattern, allows use of standard peripheral devices such as video tape recorders, video discs, etc. Before turning to the detailed description of the video A-trace display system, it will be helpful for future reference to note that the display boundaries 14a–d define a window within which the A-trace is displayed. This window referred to later in the description, has boundaries which are offset from the edges of the viewing screen for visual clarity; the beginning of the A-trace is thus offset from the initial position of the scanning beam just subsequent to its retrace.

FIG. 2 is a block diagram of the video A-trace system of the present invention. For the sake of clarity, means for generating the various timing signals have been omitted, since many such circuits are known in the art and are peripheral to the present discussion.

DATA LOADING INTO MEMORY

The incoming echos are first quantized by level and converted to a digital form by means of a video analog/digital converter (not shown). The quantizing levels are determined by pre-programmed values which may be varied by the user. The output signal is provided by a plurality of output lines which respectively indicate whether successively sampled instantaneous levels of the echo are higher or lower than the pre-programmed values. Further details concerning the video analog/digital converter may be found in our co-pending U.S. Patent Application Ser. No. 848,988, entitled "Computerized Ultrasound Scanner with Technique Select", filed concurrently herewith, assigned to the assignee hereof and hereby incorporated by reference. The digitized signals thus produced are inputted to the video A-trace converter, hereinafter described, which encodes the signal into a data format suitable for storage in memory, writes the data into a high speed memory, and reads the data out of memory at a speed suitable for video display.

In general, the period between launched pulses is divided into a number of intervals by timing means, represented in the Figures as LCLK. The number of intervals is a function of scale factor and may typically be 400. At each clock pulse, the peak level of the return echo during the previous clock period is sampled and written into a unique memory address. The address is incremented and the operation repeated. After the A-trace has been digitized and stored, it is possible to read the information out of memory at a different rate by incrementing the address and accessing the memory at a different speed. Accordingly, second timing means, hereinafter referred to as DCLK, or display clock, is preferably provided for reading the data out of memory. The operation and configuration of the presently disclosed embodiment is more easily explained by first considering the writing of data into memory and then considering the reading of data for display. This approach will necessitate alternating references to the various figures; for clarity, corresponding signals and components are identically referenced throughout the figures.

Figure 2B:
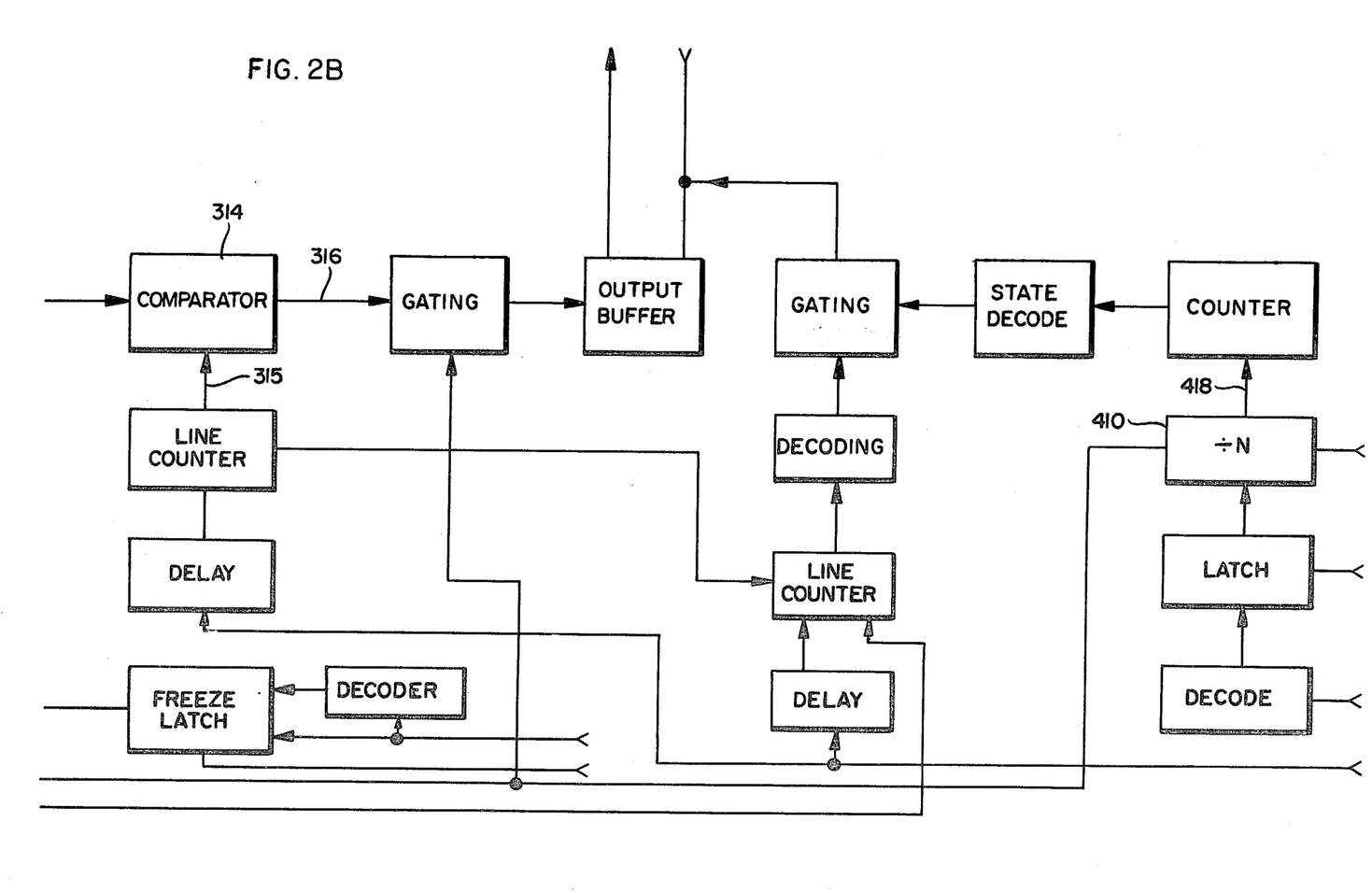
Figure 3:
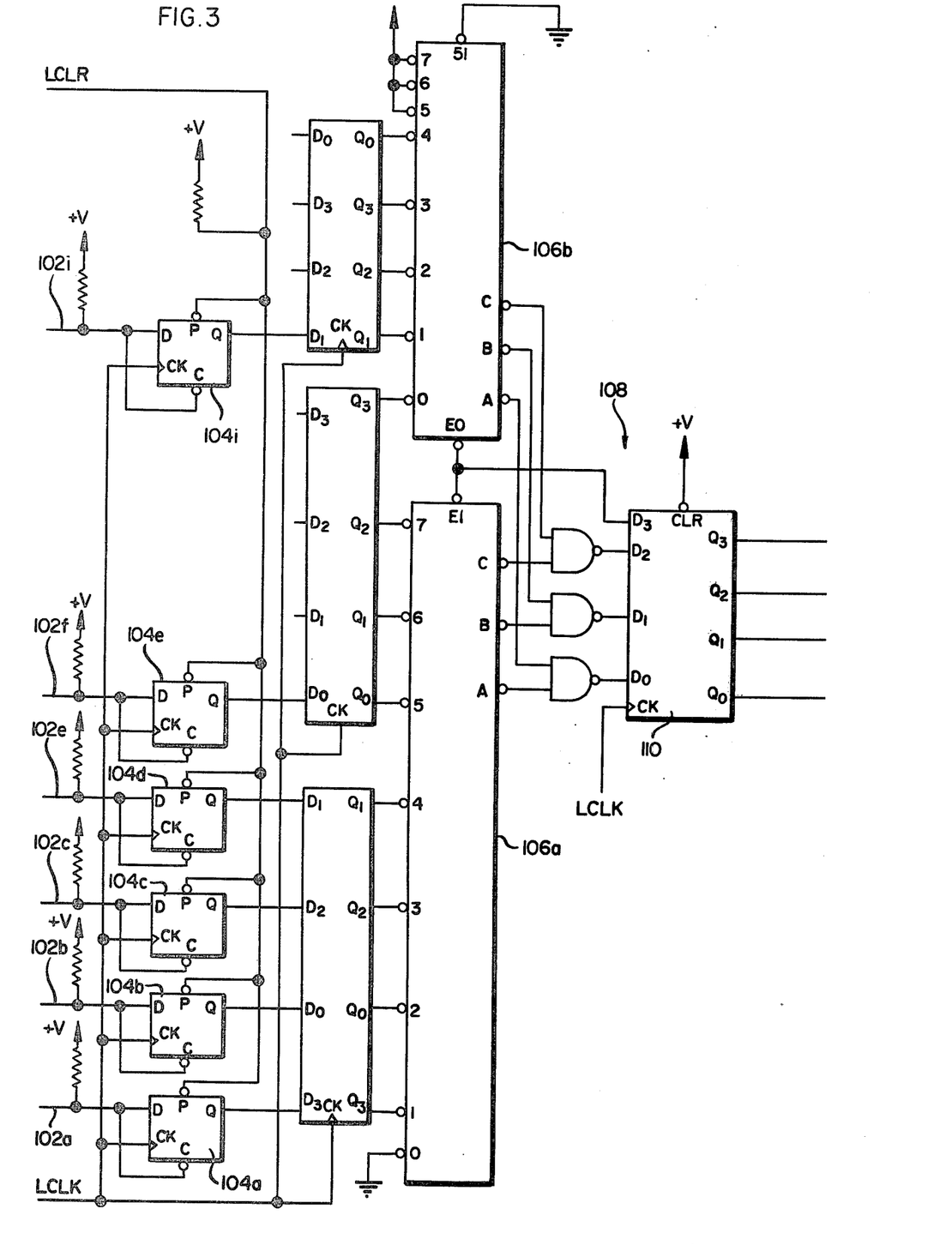
FIGS. 3-6 are schematic representations showing the preferred embodiment of the system in greater detail.
Figure 3A:
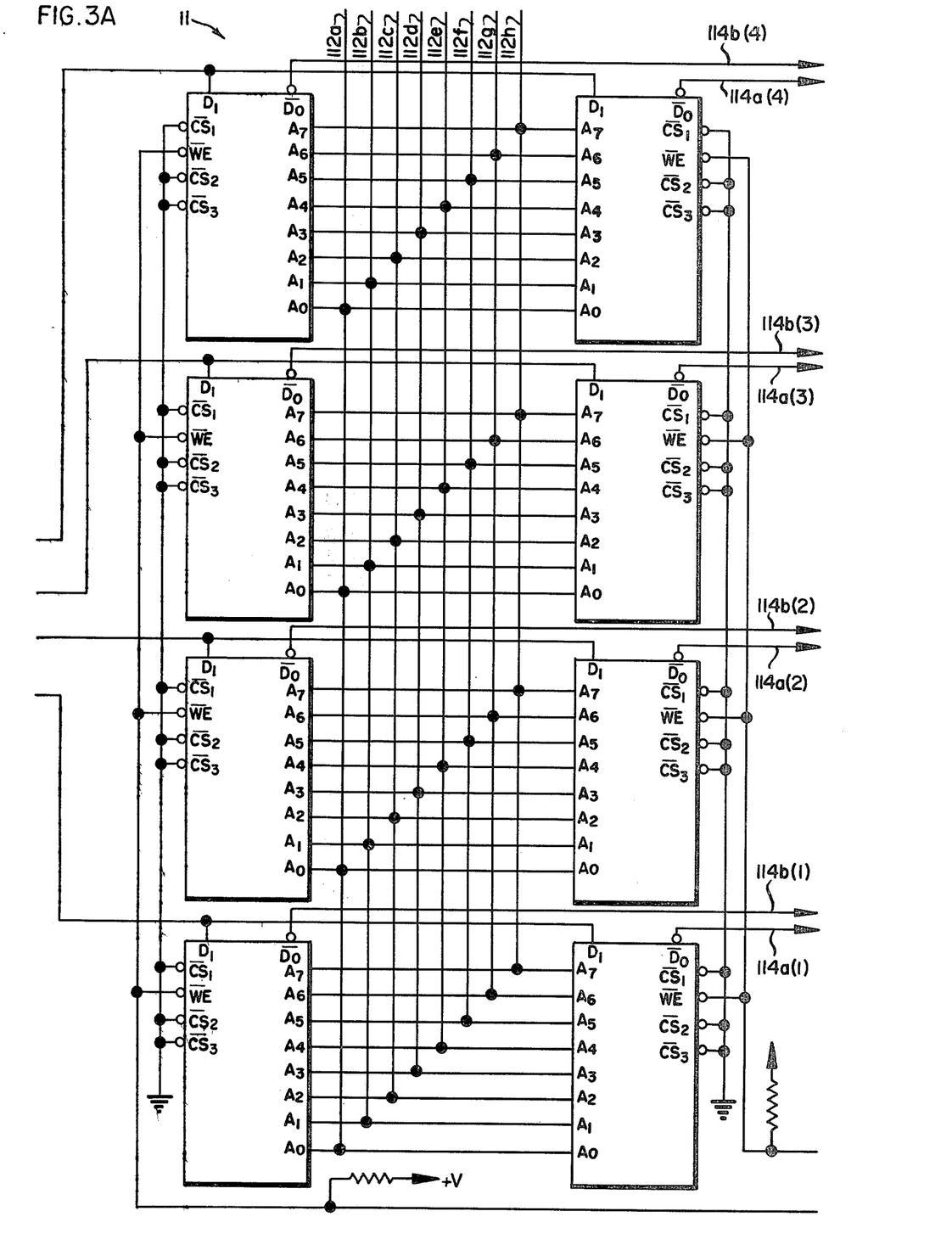

FIGS. 2A and 2B form a block diagram of the video A-trace converter of the present invention and may be utilized in conjunction with the remaining figures to obtain a general overview. As shown therein, and in more detail in FIG. 3, the quantized signals 102 from the video analog/digital converter (not shown) are sampled by input latch means 104 at a rate determined by LCLK. In practice, twelve quantizing levels and, consequently, twelve input latches are employed, although only six are shown in FIG. 3 for clarity. The pulse rate of LCLK is correlated with the depth of pulse penetration into the body, and is conveniently set at 1 pulse/mm. A change in pulse rate to 1 pulse/0.5 mm. would thereby result in a magnification of the A-trace where greater detail is necessary. The sampled values are clocked into priority encoders 106 which convert the twelve bits to a four-bit, binary-coded data work 108 which indicates the number of active lines 102. The four-bit word 108, representing the echo amplitude value, is then clocked into latch means 110 which holds word 108 for writing into memory at the appropriate time.

Memory means 111 is a random access memory array which receives address signals over lines 112 and passes output data over lines 114. At each LCLK pulse the peak reflection value during the proceeding interval is written as data into memory. By addressing the memory in a predetermined sequence, the data will be stored, for later access, in a manner by which the video elements of each video line will be correctly scanned to provide either black or white spots forming, in total, the A-trace. The manner by which address information is generated may be more readily appreciated by reference to FIG. 3 in conjunction with FIG. 1.

WRITE ADDRESS GENERATION

Figure 4:
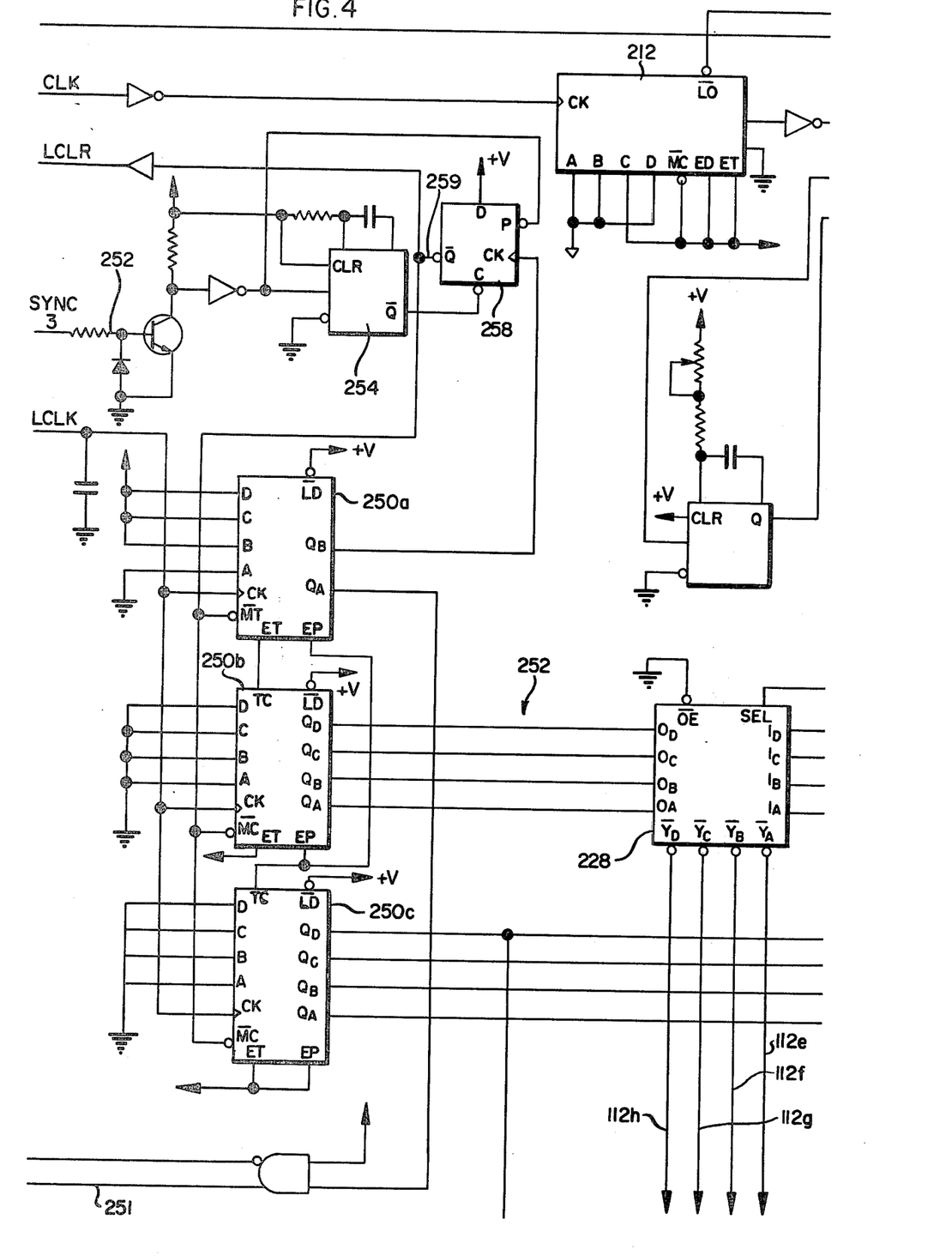
Figure 4A:
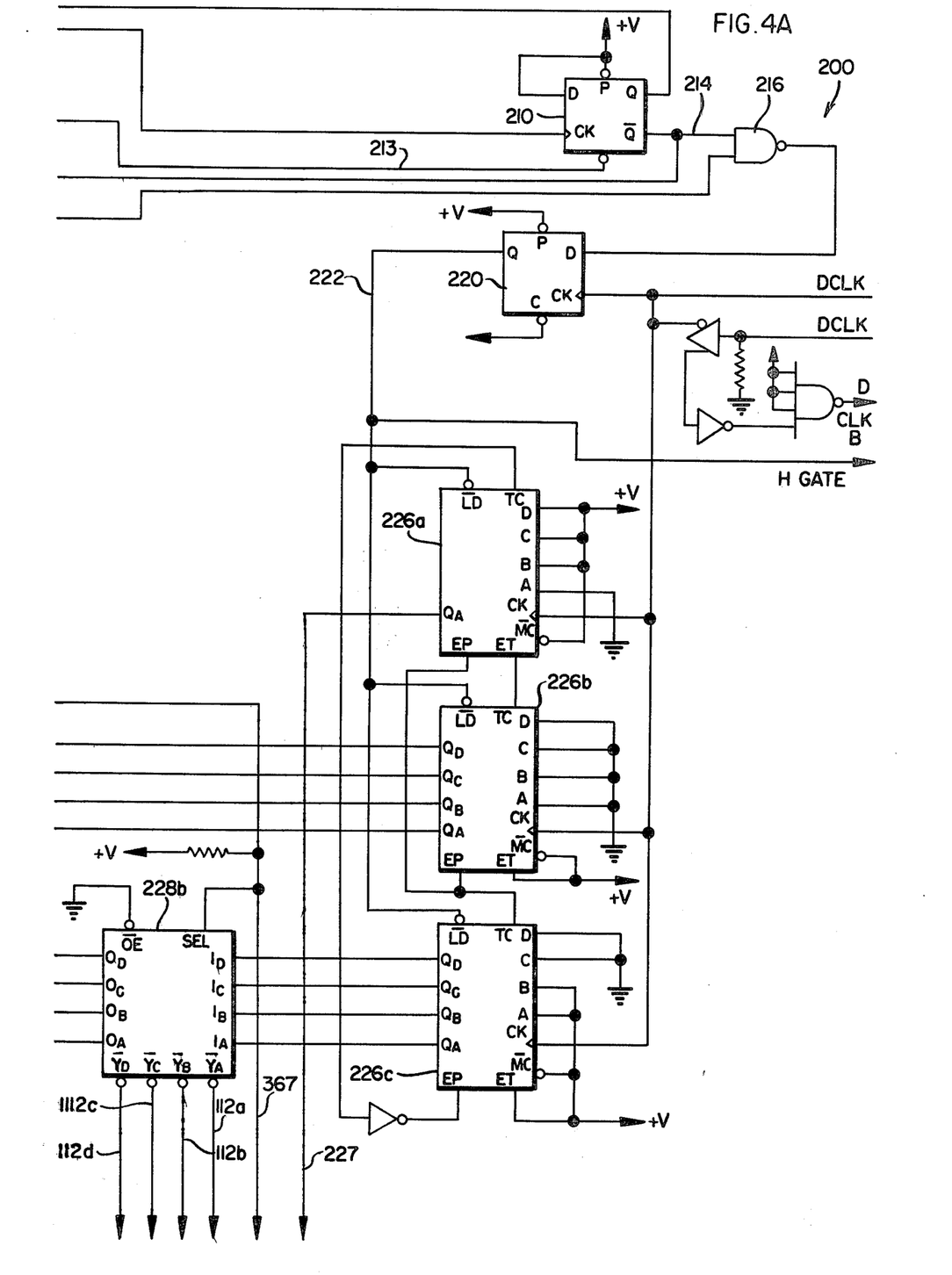

FIG. 4 shows the preferred address-generating circuitry generally indicated in FIG. 2. READ and WRITE addresses are separately generated so that the respective accessing rates may be independently optimized. Turning first to the WRITE address, the object is to permit the writing into memory of an entire video line at a time for the subsequent displaying of that line on a video monitor. As shown generally in FIG. 2, and in more detail in FIG. 4, the WRITE address circuitry comprises counter-enabling logic 254, 258 and an address counter 250. The counter-enabling logic 254, 258 functions to continuously clear the WRITE counters 250 until the presence of the SYNC 3 signal, indicative of the presence of data to be written into memory, is applied to the triggering of a one shot multi-vibrator 254. The inverted output of the one shot 254 clears a flip-flop 258 which, in turn, ceases the clearing of the counters 250a–c. The counters 250a–c accordingly count towards their terminal count at a clock rate determined by LCLK. The address-representative output bits 252 from counter are applied to one set of input terminals $O_A$–$O_D$ of an address multiplexer 228 which is responsive to a mode-select signal 230, details of which are further described hereinbelow, to select the WRITE addresses as its output 112a–h. Accordingly, each sampled value of the returning echo is assigned a unique memory address in a pre-arranged order for later access during the READ sequence hereinafter described.

READ address counter means 226.

As may be appreciated from the foregoing description, the data has been written into memory at each LCLK pulse. During the time intervals between these pulses, the disclosed system functions to read data out of memory for video display. As will be apparent from the following description, the data is read out of a rate determined by DCLK, with the memory being accessed in a predetermined sequence to read out the contents of the memory during each video line.

READ ADDRESS GENERATION

The manner by which proper READ addresses are applied to the memory matrix 111, is discussed with reference to FIG. 4. The READ address circuitry comprises counter-enabling logic 200 and an address counter 226. As shown in FIG. 4, the counter-enabling circuitry comprises a flip-flop 210 coupled at its inverted output to one input of an AND gate 216, and at its non-inverted output to the LOAD terminal of a counter 212. The counter 212 is coupled through an inverter to the CLEAR terminal of the flip-flop 210. The inverted output of the flip-flop 210 is additionally coupled to the triggering input of the AND gate 216. The AND gate 216 is, in turn, coupled to the DATA terminal of a flip-flop 220 which is clocked by the timing signal DCLK to enable the READ counters in a manner herein set forth.

The counter-enabling circuitry defines the time "window" during which the video beam is within the display boundaries 14b, d; during this time the data for a video line is accessed from memory. The commencement of the "window" is referenced to the commencement of the video line by a horizontal drive signal HDR produced at a central processing unit to indicate the retracing of the video scan beam. Accordingly, the window commences after a brief delay to enable the displayed A-trace to be spaced from the left edge of the video screen, as shown in FIG. 1. To initiate the video window, the flip-flop 210 is responsive to the horizontal drive signal HDR to load the counter 212. The counter 212 is thereby loaded with a preselected number and counts towards its terminal count. The carry-signal 213, consequently generated, clears the flip-flop 210 to initiate the window via an enabling signal 214 at one input of the AND gate 216. The signal 214 is additionally inputted to the triggering input of a one shot 218, which undergoes an output state change in a direction which enables the AND gate 216. The one shot 218 maintains the state change for a predetermined period of time, as determined by adjustment means such as a potentiometer R1 and thereafter returns to its initial state, thereby disabling the AND circuit 216, signifying the termination of the window. The flip-flop 220 thereafter functions to synchronize the commencement and termination of the window with the occurrence of DCLK. The output 222 of flip-flop 220 provides a horizontal gating signal 222. When in the normal state, the signal 222 loads the READ address counter 226 with a predetermined number. When signal 222 changes the active state, the counters 226 increment at a rate determined by DCLK from the loaded value, until the termination of the window, at which time the signal 222 returns to its normal state, and the counters 226 are reloaded. The outputted count serves as the lead address signal to the memory.

DATA DISPLAY

Figure 5:
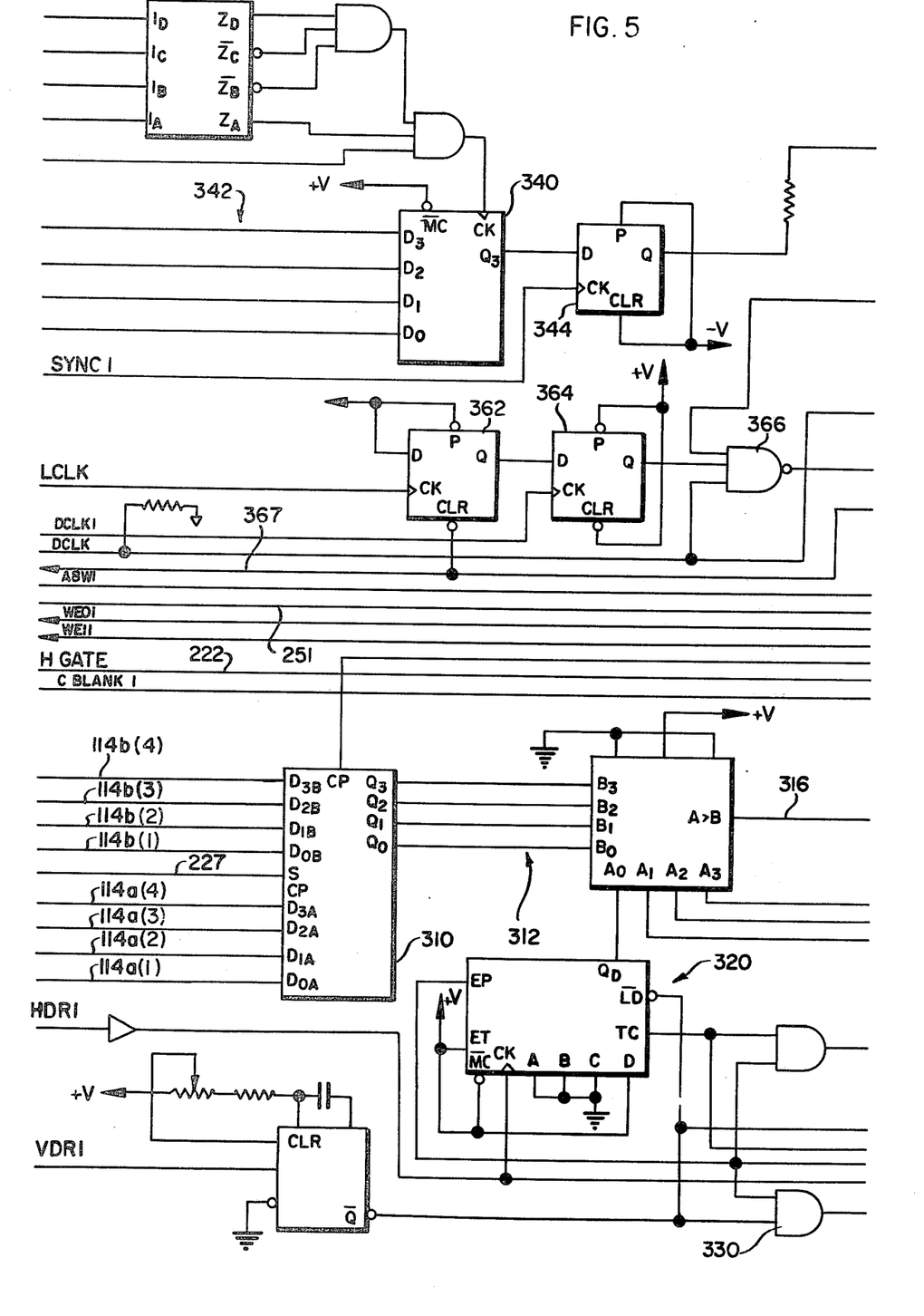
Figure 5A:
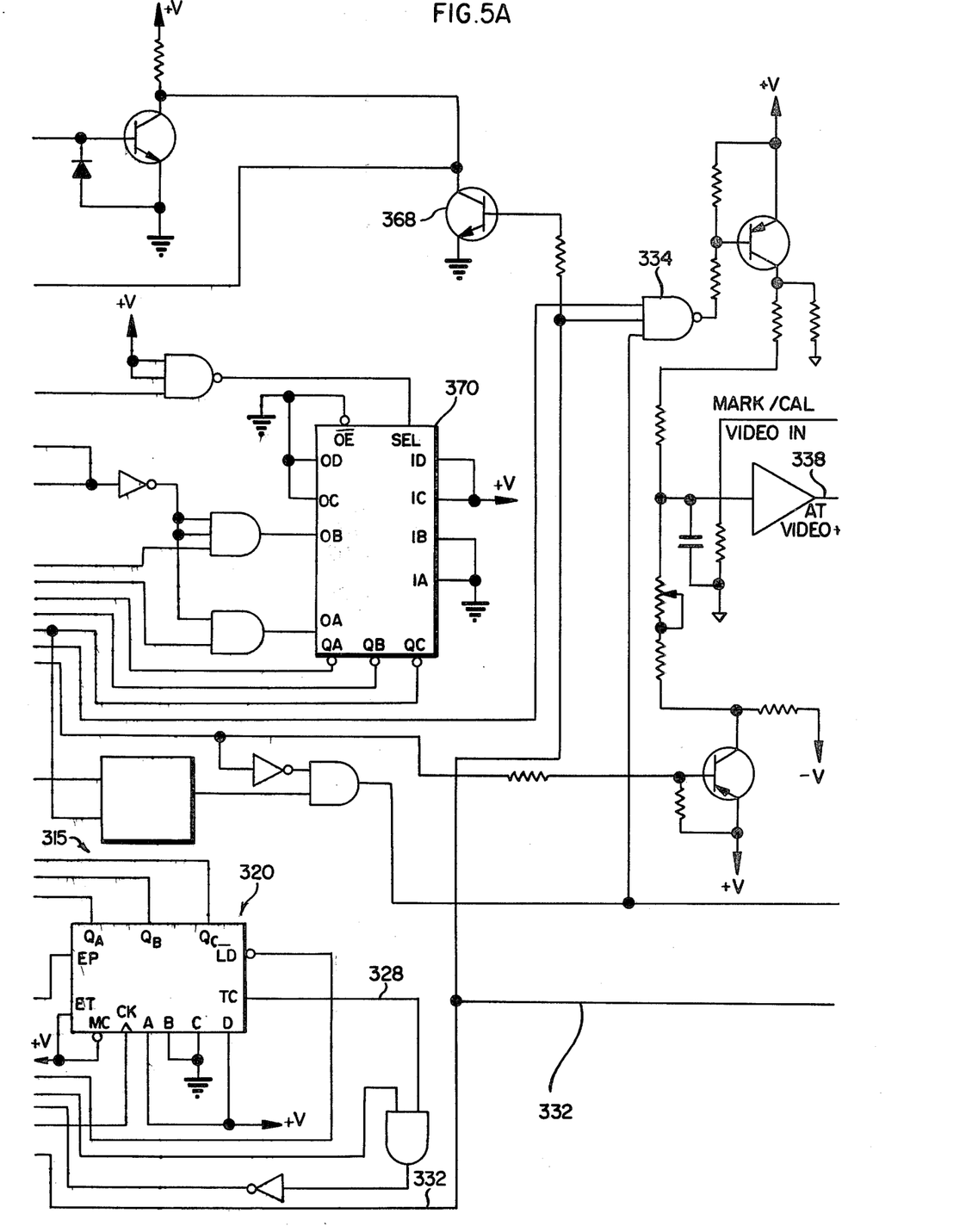

Turning next to FIG. 2 for a general overview and to FIG. 5 for a more detailed appreciation of data retriving circuitry operation. The data output signals 114 (FIG. 3) from the addressed memory location are applied as shown in FIG. 5 to the input terminals of a multiplexer 310. It may be noted that the output signals from the right side of the matrix 111 (FIG. 3) are applied to one bank of multiplexer 310 inputs while the data from the left side of the memory matrix 111 is applied to the second bank of multiplexer 310 inputs. The multiplexer 310 is responsive to the select signal 227 which, is produced by the READ counters 226 as part of the memory address.

It may be helpful to remember that the output signal 312 from the multiplexer 310 represents quantized sampled signal levels of the returning echo reflections, where the sampling rate was determined by LCLK. If the contents of the memory are read out during every video line in the sequence in which they were stored and converted to an intensity modulated signal in a format compatible with the raster scan of the video beam, a video display of the A-trace is produced. Turning briefly to FIG. 1, it may be appreciated that each video line of the graphically displayed A-trace will comprise both light and dark elements. For example, each point below the boundary of the graph may appear as a white video element, with the background appearing black. Since the ordinate of the A-trace represents the amplitude of the reflection, it is obvious that the intensity (i.e. black or white) of each picture element in a video line will depend upon whether the amplitude of the pulse reflection at the return time represented by the picture element's abscissa value is greater to or less than the ordinate value associated with the particular video line. Returning to FIG. 5, it may be seen that the data signal 312 from the multiplexer 310 is applied to the inputs of a comparator 314 and compared to threshold levels 315 produced by video line counters 320. The line counters 320 function to produce a threshold level corresponding to the ordinate value associated with the video line in FIG. 1A. In the described embodiment, the comparator output 316 will eventually produce a white picture element if the signal 312 is greater than the threshold 315, and will produce a black picture element if the signal 312 is less than the threshold 315. Consequently the area under the A-trace will contrast with the background. Naturally, the relationship may be reversed so that the area under the A-trace of FIG. 1A would appear black against a white background.

The operation of the line counters is apparent from FIG. 5. Briefly, the counters 320 are responsive to a vertical drive signal VDR that signifies the verfical retrace of the video scanning beam. The signal VDR triggers a one shot multi-vibrator 326, the output signal 324 of which enables the counter 320 to count from a loaded value towards a terminal count when clocked by the signal HDR, indicative of the horizontal retrace of the video scanning beam. The counter 320 is configured to increment once every video line and to change its output every eight video lines. Upon reaching its terminal count, the counter 320 is disabled by its "carry" signal 328.

The A-trace converter includes circuitry to insure that the data is displayed within the display portion of the video screen defined by the boundaries 14a–d (in FIG. 1) by producing vertical and horizontal gate signals. The horizontal state signal 222 is described above. The vertical gate signal is produced a finite time interval after the vertical retrace of the video beam to insure that the A-trace is displayed within the boundaries 14a, c. The "carry" signal 328 from the line counter 320, signifying the completion of the window in the vertical direction is accordingly coupled along with a time-delayed vertical drive pulse 324 which indicates the initiation of the window vertically, to respective inputs of an AND gate 330.

The output signal 316 from the comparator 314 is accordingly coupled with the horizontal gate signal 222 and the vertical gate signal 322 respective inputs of an AND gate 334, which produces, as its output, a properly timed video beam modulating signal 338.

It may be appreciated that the original data signal was written into memory at a clock rate corresponding to fixed incremental depths into the examined body. Therefore each clock pulse on READ also corresponds to that depth and depth calibration is accordingly maintained regardless of the DCLK rate; a different DCLK rate will accordingly result in the display of a different body depth along the horizontal direction, thereby creating a change in the scale factor.

ELECTRONIC CALIPER AND SELECTIVE GAIN DISPLAY

As indicated earlier in this disclosure, the video display of the A-trace lends itself to operator-actuable video calipers which may be utilized to accurately measure the displayed distance into the body of the discontinuity-generating reflections as well as the difference in return times of a pair of discontinuities. It may be appreciated that since each DCLK pulse corresponds to a fixed distance, that counting these pulses enables measurement of distances.

Figure 6:
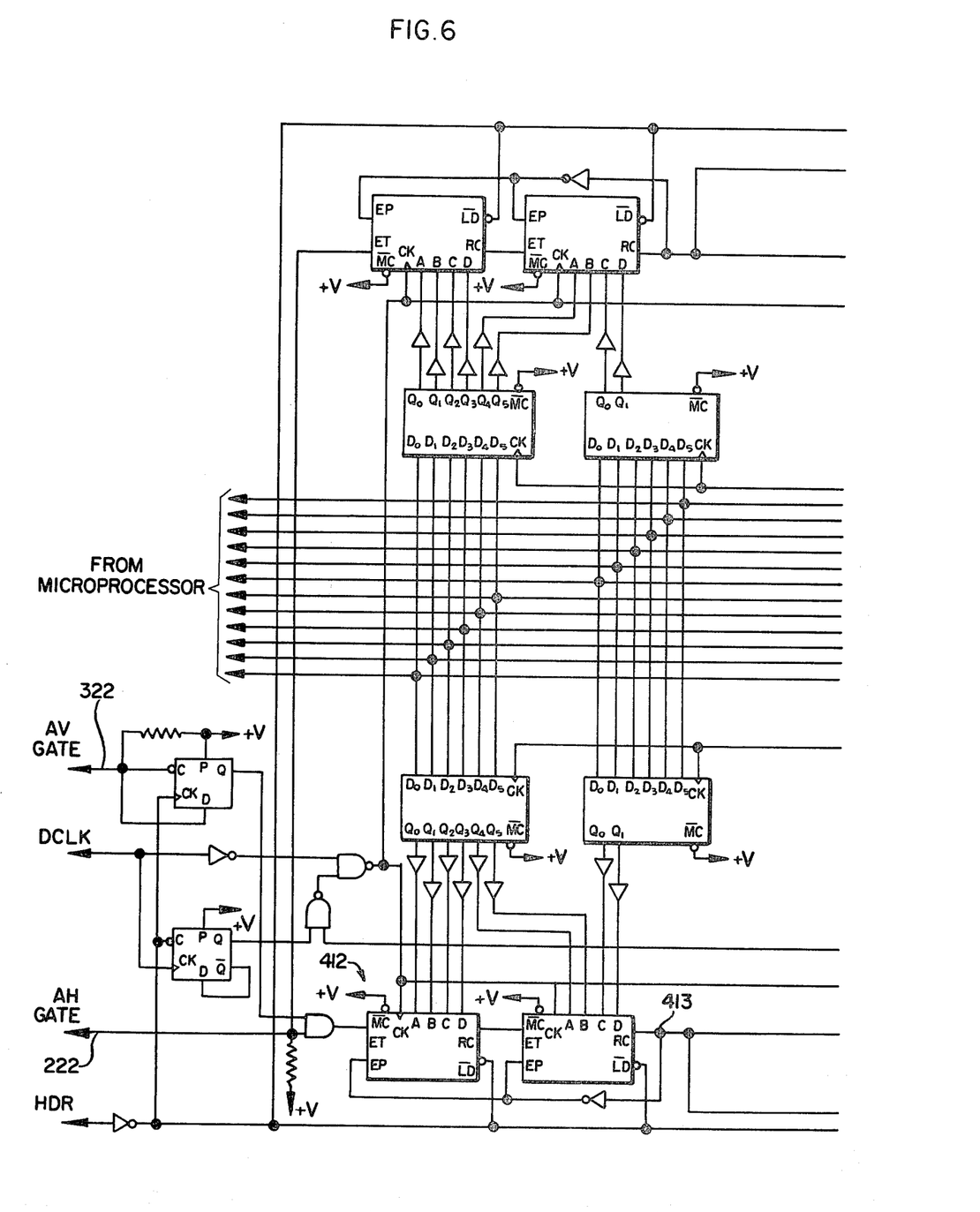
Figure 6A:
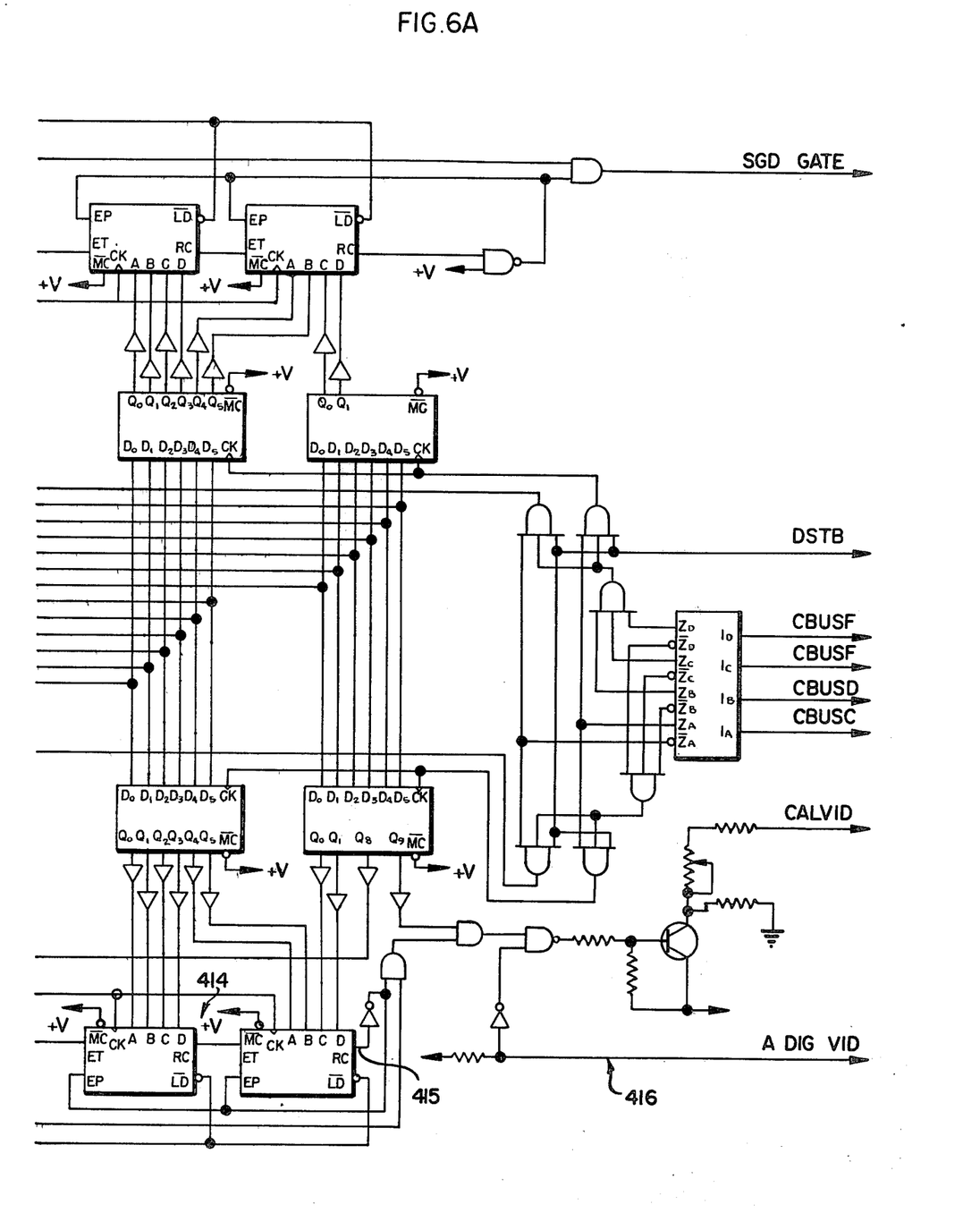

FIG. 6 schematically illustrates the circuit for producing the caliper. The horizontal and vertical gate signals 222, 322 pass through enabling logic which produce an enabling signal, synchronized with DCLK, to a pair of counters 410, 412. The counter 412 is a caliper delay counter which provides a variable delay from the beginning of the A-trace to the beginning of the caliper so that the caliper may be moved along the abscissa of the A-trace as desired by the operator. The counter 412 is incremented by DCLK, which is synchronized with the commencement of the video line, and enables the caliper-producing circuitry at its terminal count. The caliper producing circuitry comprises a caliper spacing counter 414 which, as indicative hereinbelow, counts a variable number corresponding to the width of the caliper. The "carry" dignals 413, 415 from the counter 412, 414 are coupled into an output stage 416.

The delay produced by the counters is determined by a variable preloaded count which is derived by a microprocessor in accordance with pre-programmed instructions in response to the wishes of the operator. The counters are loaded in response to the horizontal retrace signal HDR at the commencement of each video line at the same initial point, and the delay counter begins counting at the start of the A-trace display time indicated by gate signal 222. Upon reaching the terminal count, the counter 412 is disabled by its "carry" output 413 which Returning now to the mode select signal 230, mentioned briefly above with respect to the multiplexer 228, attention should be directed to FIG. 5 and, more particularly to the WRITE Request Logic 360 therein, which comprises a pair of flip-flops 362, 364, an AND gate 366 and a multiplexer 370. The mode select signal 230 may be seen to be the output signal from an AND gate 366 which serves to synchronize production of the mode select 230 with the timing signal LCLK; during time intervals in which data is not to be read for display. Accordingly, the flip-flops 362, 364 are responsive to LCLK and to the absense of a DCLK pulse to enable the AND gate 366. A second input of the AND gate 366 is coupled to transistor 368, which disables the AND gate, as hereinafter described to insure that no data may be written into memory in those addresses corresponding to video display positions lying outside the boundaries 14a-d and 22a-d (FIG. 1). This latter function is provided by means of transistor 368 which is responsive to a vertical gating signal 332, hereinafer described. The second input is additionally coupled to "freeze" circuit 372 which is actuable by the operator request to prevent the writing of new data into memory.

The mode select signal 230 is additionally applied to the multiplexer 370 to respectively produce one of two possible WRITE enable signals WE0, WE1 which, by reference to FIG. 3, may be seen as being applied to the memory matrix 111 in order to cause the writing of the data held in the latch 110 at the address specified by the WRITE address counter outputs 112a-h.

DATA RETRIEVAL AND DISPLAY

Having thus stored the echo information in memory, discussion is next turned to the manner by which the data is read from memory for video display. Turning first to the READ address, the object is to read the data associated with successive video elements of each video line on a line-by-line basis. As shown in FIG. 2, and in more detail in FIG. 4, the READ address circuitry comprises the counter-enabling logic 200 and additionally enables the counter 414 and enables the caliper display. The counter 414 now counts toward its terminal count. Upon reaching that count, it is disabled by its "carry" output 415, which also disables the caliper display.

The "carry" outputs 413, 415 from the counters 412, 414 are coupled to respective inputs of an AND gate 418 to produce a "window" during which time the caliper is to appear. The output of the gate 418 is similarly coupled to respective inputs of a second AND gate 420 along with a microprocessor signal indicative of an operator-induced "caliper request". As an added feature, the caliper-producing circuitry is overridden by the A-trace circuitry so that the caliper video will not appear where the A-trace video is.

The counters 412, 414 hold their terminal counts state until the next load pulse HDR where, at which time they are reloaded and the counting sequence commences once again.

We claim:

1. For use with an ultrasonic diagnostic system of the type including
    means for launching an ultrasonic pulse into the diagnosed body,
    means for detecting emerging pulse reflections from the body and responsive thereto to produce respective amplitude-indicative electronic signals, and
    video means including a photoresponsive surface and means for repeatedly sweeping a scanning electron beam over a plurality of generally parallel video lines on the surface to define a multi-lined video field,
    an A-trace display system for modulating the electron beam comprising:
    memory means having uniquely addressed locations for storing digital values;
    means for storing in a predetermined succession of memory locations respective digital values indicative of pulse-reflection amplitudes at respective time-intervals subsequent to the launching of a pulse;
    means responsive to the initiation of a video line to access the successive memory locations in a sequence which permits retrieval of the values in a reconstructed time-phase relationship;
    means for producing a reference signal having a value which is generally proportional to the position within the video field of the video line being scanned;
    comparator means for producing successive beam-modulating signal respectively indicative of whether the successive signal values are greater than or less than the reference signal, the beam-modulating signal being such that the scanning beam selectively strikes the video line elements above or below the video line having a relative position within the video field generally proportioned to the relative amplitude of the pulse reflection.

2. The video display system of Claim 1 including means for producing a first timing signal wherein the memory access means includes
    counter means incremented at a rate determined by the first timing means to count from an initially preloaded value towards a terminal count for producing an address signal, and means responsive to the commencement by the video beam of a new video line to preload the counter means, the count between the initial and terminal values being related to the scan time of the video line so as to address during the scanning of the video line the memory locations containing the data to be displayed.

3. The video display system of Claim 2 wherein the counter means is adapted to address all the memory locations containing data to be displayed during the scanning of each video line in the A-trace field.

4. The video display system of Claim 1 including means responsive to the commencement of each video line for producing a gate signal delayed therefrom, the gate signal being of shorter duration than the time remaining at its initiation for the video beam to complete the video line, and means responsive to the gate signal for enabling the counter means, whereby horizontal display boundaries are produced.

5. The video display system of Claim 4 wherein the video display means includes means for sweeping the video beam in a raster pattern, and wherein the gate signal producing means includes means for producing a bistable output signal, one of the states serving as a horizontal drive signal indicative of the horizontal retrace of the video beam, bistable signal producing means responsive to the horizontal drive signal to produce a time-delayed state change of said shorter duration, logic gate means responsive to the horizontal drive signal and the time-delayed signal to produce the counter-enabling gate signal.

6. For use with an ultrasonic diagnostic system of the type including means for lauching an ultrasonic pulse into the diagnosed body, means for detecting emerging pulse reflections from the body and responsive thereto to produce respective amplitude-indicative electronic signals, and video display means including a photosensitive surface and means for repeatedly sweeping a scanning electron beam over a plurality of generally parallel video lines on the surface to define a multilined video field, a video A-trace display system comprising:

first timing means responsive to the launching of an ultrasonic pulse for producing a first series of timing pulses;

memory means having uniquely addressed locations for storing digital values;

means responsive to said first timing means and coupled to the detecting means to sample the amplitude-indicative signals at successive discrete time subsequent to the pulse launching and to apply the successively sampled signals as digital data to the memory means;

first means responsive to the first timing means for successively accessing the address locations to permit the storing of the successively sampled data in respective locations;

second means responsive to the second timing means for successively accessing at least a portion of the locations accessed by the first means, said portion being accessed during each video line scan; and means responsive to the accessed data values for modulating the electron beam.

7. The ultrasonic diagnostic system of claim 6 including means responsive to the commencement of each video line and synchronized with the scanning thereof by the video beam to sequentially apply the successively retrieved data to the comparator means at a rate by which the last-displayed value is applied generally proximate to the end of the video line.

8. The ultrasonic diagnostic system of claim 7 including counter means responsive to the pulses of the second series of pulses to count from an initial value to a terminal value, the count value being uniquely related to a respective memory address, and means responsive to the initiation of each video line to load the counter means with the initial number, whereby the second access means cycles through the addresses containing the displayed information during each video line.

9. The ultrasonic diagnostic system of claim 6 including first counting means incremented by the first series of pulses from an initially loaded count value to a termination count value, to produce WRITE address signals, second counting means incremented by the second series of pulses from an initially loaded count value to a termination count value to produce READ address signals multiplexing means selectively coupling the READ and WRITE address signals to the memory means in response to a respective state of a bistable mode signal; and means for producing the bistable mode signal, including means responsive to the first series of timing pulses to produce a first request signal, means responsive to the first request signal to produce a second request signal at an appropriate time relative to a pulse of the second series, and means responsive to a subsequent pulse of the second series to couple the WRITE address signals to the memory means.

* * * * *